US007060709B2

(12) United States Patent
Cooperstone et al.

(10) Patent No.: US 7,060,709 B2
(45) Date of Patent: Jun. 13, 2006

(54) METHOD OF TREATING HEPATIC FIBROSIS

(75) Inventors: Brenda Cooperstone, Bryn Mawr, PA (US); Robert Clare, Wayne, PA (US); George Stanley, Surrey (GB)

(73) Assignee: Wyeth, Madison, NJ (US)

( * ) Notice: Subject to any disclaimer, the term of this patent is extended or adjusted under 35 U.S.C. 154(b) by 308 days.

(21) Appl. No.: 10/767,824

(22) Filed: Jan. 29, 2004

(65) Prior Publication Data

US 2004/0242621 A1    Dec. 2, 2004

Related U.S. Application Data

(60) Provisional application No. 60/445,517, filed on Feb. 6, 2003.

(51) Int. Cl.
*A61K 31/44*    (2006.01)
(52) U.S. Cl. ..................................... 514/291
(58) Field of Classification Search ............... None
See application file for complete search history.

(56) References Cited

U.S. PATENT DOCUMENTS

| | | | |
|---|---|---|---|
| 3,929,992 | A | 12/1975 | Sehgal et al. |
| 3,993,749 | A | 11/1976 | Sehgal et al. |
| 4,401,653 | A | 8/1983 | Eng |
| 4,885,171 | A | 12/1989 | Surendra et al. |
| 5,078,999 | A | 1/1992 | Warner et al. |
| 5,080,899 | A | 1/1992 | Sturm et al. |
| 5,100,899 | A | 3/1992 | Calne |
| 5,206,018 | A | 4/1993 | Sehgal et al. |
| 5,286,730 | A | 2/1994 | Caufield et al. |
| 5,286,731 | A | 2/1994 | Caufield et al. |
| 5,288,711 | A | 2/1994 | Mitchell et al. |
| 5,321,009 | A | 6/1994 | Baeder et al. |
| 5,362,718 | A | 11/1994 | Skotnicki et al. |
| 5,387,589 | A | 2/1995 | Kulkarni |
| 5,496,832 | A | 3/1996 | Armstrong |
| 5,516,781 | A | 5/1996 | Morris et al. |
| 5,561,138 | A | 10/1996 | Armstrong |
| 5,665,772 | A | 9/1997 | Cottens et al. |
| 6,277,983 | B1 | 8/2001 | Shaw et al. |
| 6,670,355 | B1 | 12/2003 | Azrolan et al. |
| 2002/0061903 | A1* | 5/2002 | Zhu .................. 514/291 |
| 2002/0061904 | A1* | 5/2002 | Zhu et al. ............. 514/291 |
| 2004/0077677 | A1* | 4/2004 | Ashraf et al. .......... 514/291 |

FOREIGN PATENT DOCUMENTS

| | | |
|---|---|---|
| EP | 0525960 B1 | 3/1996 |
| WO | WO 01/97809 A2 | 12/2001 |
| WO | WO 03/077915 A1 | 9/2003 |

OTHER PUBLICATIONS

STN Registry File, RN:162635-04-3 Rapamycin, 42-[3-hydroxy-2-(hydroxymethyl)-2-methylpropanoate], entered STN on May 3, 1995.*

National Library of Medicine—Medical Subject Headings, 2006 MeSH, Supplementary Concept Data, for Substance "CCI 779".*
Staruch et al, FK506 and Rapamycin Inhibit Murine T Cell Activation Through Different Mechanisms, The FASEB Journal, vol. 3, No. 3 3411, (1989).
Sehgal et al, Rapamycin (AY-22, 989), A New Antifungal Antibiotic, II. Fermentation, Isolation and Characterization, The Journal of Antibiotics, vol. XXVIII No. 10, pp. 727-732 (Oct. 1975).
Vezina et al, Rapamycin (AY-22,989), A New Antifungal Antibiotic I. Taxonomy of the Producing Streptomycete and Isolation of the Active Principle, The Journal of Antibiotics, vol. XXVIII No. 10, pp. 721-726 (Oct. 1975).
Baker et al, Rapamycin (AY-22,989), A New Antifungal Antibiotic, III. In Vitro and In Vivo Evaluation, The Journal of Antibiotics, vol. XXXI, No. 6, pp. 539-545, (Jun. 1978).
Martel et al, Inhibition of the Immune Response by Rapamycin, a New Antifungal Antibiotic, Can. J. Physiol. Pharmacol. vol. 55, pp. 48-51 (1977).
Dumont et al, Rapamycin Blocks the Immunosuppressive Effect of FK506 But Not That of Cyclosporin A, FASEB Journal, 5256, vol. 3, No. 4, (1989).
R. Y. Calne et al, Prolonged Survival of Pig Orthotopic Heart Grafts Treated with Cyclosporin A, Lancet, pp. 1183-1185, (Jun. 3, 1978).
Shibata Norikuni, *Antifibrosis effect of interferongamma (IFNgamma) and rapamycin (Rapa) in immortal human hepatic stellate cells*, Database Biosis Online!, 2002, pp. 185-197, Database accession No. PREV200300151275, ISSN: 0386-5924, vol. 28, pp. 185-197, Biosciences Information Service, Kawasaki Igakkai Shi [Abstract].
S. Jain, et al., *Rapamycin Reduces Expression of Fibrosis-Associated Genes in an Experimental Model of Renal Ischaemia Reperfusion Injury*, Transplantation Proceedings, Feb. 2001, pp. 556-558, vol. 22, No. 1-2, ISSN: 0041-1345, Elsevier Science, Inc., New York, NY.
Yoshihide Arisaka, *Effects of interferon-.gamma. and rapamycin on transforming growth factor-.beta.-induced liver fibrosis in an organotypic slice culture*, Database Chemabs Online!, 2003, pp. 597-603, Database accession No. 2004:146496, ISSN: 0029-0424, vol. 62(11), Nihon Daigaku Igakkai [Abstract].

(Continued)

Primary Examiner—Raymond J. Henley, III
(74) Attorney, Agent, or Firm—Arnold S. Milowsky

(57) ABSTRACT

This invention provides the use of rapamycin 42-ester with 3-hydroxy-2-(hydroxymethyl)-2-methylpropionic acid (CCI-779) in the treatment or inhibition of hepatic fibrosis and hepatic cirrhosis.

10 Claims, No Drawings

OTHER PUBLICATIONS

L. Lopez-Lazarro, et al., F. Lokiec, et al., H.C. Swaisland, et al., U. Mayer, et al., L. Plasswilm, et al., G. Cartei, et al., F. Lokiec, et al., M. Airoldi, et al., J. Boni, et al., O. Tomoyuki, et al., O. Juan, et al., T. Oe, et al., *Pharmacokinetics* poster session (12 individual poster titles), European Journal of Cancer, Oct. 2001, pp. S66-S69, vol. 37, Pergamon Press, Oxford, GB [Posters].

Shibata et al, Establishment of an Immortalized Human Hepatic Stellate Cell Line to Develop Antifibrotic Therapies, Cell Transplantation, vol. 12, pp. 499-507, (2003).

Friedman et al, The Virtuosity of Hepatic Stellate Cells, Gastroenterology, vol. 117, No. 5, pp. 1244-1246, (Nov. 1999).

Zhu et al, Rapamycin Inhibits Hepatic Stellate Cell Proliferation in Vitro and Limits Fibrogenesis in an In Vivo Model of Liver Fibrosis, Gastroenterology 117, 5, pp. 1198-1204, (Nov. 1999).

* cited by examiner

METHOD OF TREATING HEPATIC FIBROSIS

CROSS-REFERENCE TO RELATED APPLICATION

This application claims the benefit under 35 USC 119(e) of the priority of U.S. patent application No. 60/445,517, filed Feb. 6, 2003.

BACKGROUND OF THE INVENTION

This invention relates to the treatment or inhibition of hepatic fibrosis and hepatic cirrhosis.

Hepatic fibrosis can occur following chronic injury of various etiologies. As part of the wound healing response, hepatic cells produce scar tissue in the months or years following hepatic insult leading ultimately to severe fibrotic changes and a breakdown in the normal architecture of the liver, also known as cirrhosis. The primary insult can include infections, such as Hepatitis, toxins, as in Alcoholic Liver Disease, genetic abnormalities or autoimmune diseases. The presence of hepatic fibrosis can herald progression to complete liver failure with the need for a liver transplant as a life-saving procedure.

Rapamycin is a macrocyclic triene antibiotic produced by *Streptomyces hygroscopicus*, which was found to have antifungal activity, particularly against *Candida albicans*, both in vitro and in vivo [C. Vezina et al., *J. Antibiot.* 28, 721 (1975); S. N. Sehgal et al., *J. Antibiot.* 28, 727 (1975); H. A. Baker et al., *J. Antibiot.* 31, 539 (1978); U.S. Pat. No. 3,929,992; and U.S. Pat. No. 3,993,749]. Additionally, rapamycin alone [U.S. Pat. No. 4,885,171] or in combination with picibanil [U.S. Pat. No. 4,401,653] has been shown to have antitumor activity.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [*FASEB* 3, 3411 (1989); *FASEB* 3, 5256 (1989); R. Y. Calne et al., *Lancet* 1183 (1978); and U.S. Pat. No. 5,100,899]. R. Martel et al. [*Can. J. Physiol. Pharmacol.* 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

Rapamycin is also useful in preventing or treating systemic lupus erythematosus [U.S. Pat. No. 5,078,999], pulmonary inflammation [U.S. Pat. No. 5,080,899], insulin dependent diabetes mellitus [U.S. Pat. No. 5,321,009], skin disorders, such as psoriasis [U.S. Pat. No. 5,286,730], bowel disorders [U.S. Pat. No. 5,286,731], smooth muscle cell proliferation and intimal thickening following vascular injury [U.S. Pat. Nos. 5,288,711 and 5,516,781], adult T-cell leukemia/lymphoma [European Patent Application 525,960 A1], ocular inflammation [U.S. Pat. No. 5,387,589], malignant carcinomas [U.S. Pat. No. 5,206,018], cardiac inflammatory disease [U.S. Pat. No. 5,496,832], and anemia [U.S. Pat. No. 5,561,138].

Rapamycin 42-ester with 3-hydroxy-2-(hydroxymethyl)-2-methylpropionic acid (CCI-779) is ester of rapamycin that has demonstrated significant inhibitory effects on tumor growth in both in vitro and in vivo models. The preparation and use of hydroxyesters of rapamycin, including CCI-779, are disclosed in U.S. Pat. Nos. 5,362,718 and 6,277,983.

CCI-779 exhibits cytostatic, as opposed to cytotoxic properties, and may delay the time to progression of tumors or time to tumor recurrence. CCI-779 is considered to have a mechanism of action that is similar to that of sirolimus. CCI-779 binds to and forms a complex with the cytoplasmic protein FKBP, which inhibits an enzyme, mTOR (mammalian target of rapamycin, also known as FKBP12-rapamycin associated protein [FRAP]). Inhibition of mTOR's kinase activity inhibits a variety of signal transduction pathways, including cytokine-stimulated cell proliferation, translation of mRNAs for several key proteins that regulate the G1 phase of the cell cycle, and IL-2-induced transcription, leading to inhibition of progression of the cell cycle from G1 to S. The mechanism of action of CCI-779 that results in the $G_1$-S phase block is novel for an anticancer drug.

In vitro, CCI-779 has been shown to inhibit the growth of a number of histologically diverse tumor cells. Central nervous system (CNS) cancer, leukemia (T-cell), breast cancer, prostate cancer, and melanoma lines were among the most sensitive to CCI-779. The compound arrested cells in the G1 phase of the cell cycle.

In vivo studies in nude mice have demonstrated that CCI-779 has activity against human tumor xenografts of diverse histological types. Gliomas were particularly sensitive to CCI-779 and the compound was active in an orthotopic glioma model in nude mice. Growth factor (platelet-derived)-induced stimulation of a human glioblastoma cell line in vitro was markedly suppressed by CCI-779. The growth of several human pancreatic tumors in nude mice as well as one of two breast cancer lines studied in vivo also was inhibited by CCI-779.

DESCRIPTION OF THE INVENTION

This invention provides a method of using CCI-779 in the treatment or inhibition of hepatic fibrosis and hepatic cirrhosis. In particular, CCI-779 is useful in treating or inhibiting hepatic fibrosis or hepatic cirrhosis which may in part be caused by primary biliary cirrhosis; biliary cirrhosis (secondary); sclerosing cholangitis, both primary and secondary; biliary atresia; cystic fibrosis; alcoholic liver disease; cardiac cirrhosis; congenital hepatic fibrotic disorders including; drug induced hepatic fibrosis, including alcohol, methotrexate, isoniazid, vitamin a, amiodarone, perhexilene maleate, alpha methyl dopa, oxyphenistatin; infections including chronic hepatitis b and c virus, brucellosis, echinococcus, congenital or tertiary syphilis; leishmaniasis; schistosomiasis; parasitic diseases leading to hepatic cirrhosis/fibrosis; autoimmune chronic hepatitis; hereditary hemorrhagic telangiectasias; steatohepatitis; veno-occlusive disease; idiopathic portal fibrosis; metabolic/genetic diseases including genetic hemochromatosis, wilson's disease, alpha1 antitrypsin deficiency, porphyria, carbohydrate metabolism disorders, lipid metabolism disorders, amino acid metabolism disorders, urea cycle defects; Indian childhood cirrhosis; granulomatous liver disease; or polycystic liver disease.

This invention also provides a method of treating or inhibiting hepatic fibrosis or hepatic cirrhosis using 42-O-(2-hydroxy)ethyl rapamycin; the preparation of which is described in U.S. Pat. No. 5,665,772, which is hereby incorporated by reference.

As used in accordance with this invention, the term "treatment" means treating a mammal hepatic fibrosis or hepatic cirrhosis by providing said mammal an effective amount of a CCI-779.

As used in accordance with this invention, the term "inhibition" means inhibiting the onset or progression of hepatic fibrosis or hepatic cirrhosis in a mammal having or susceptible to developing such diseases by providing said mammal an effective amount of CCI-779.

As used in accordance with this invention, the term "providing," means either directly administering CCI-779 or administering a prodrug, derivative, pharmaceutical salt, or analog of CCI-779 which will form an effective amount of CCI-779 in the body.

The preparation of CCI-779 is described in U.S. Pat. No. 5,362,718, which is hereby incorporated by reference. A regiospecific synthesis of CCI-779 is described in U.S. Pat. No. 6,277,983, which is hereby incorporated by reference.

Suitable in vitro and in vivo models for hepatic fibrosis and hepatic cirrhosis have been described in conjunction with other active agents. See, e.g., J. Zhu et al, *Gastroenterology*, 117(5):1244–1246 (November 1999) and N. Shibata et al, *Cell Transplant*, 12(5):499–507 (2003).

When CCI-779 is used in the treatment of hepatic fibrosis or hepatic cirrhosis, it is the daily oral dosage is in the range of about 0.5 to about 10 mg/day. Oral infusion and intravenous infusion are the preferred routes of administration, with oral being more preferred. In another embodiment, CCI-779 (or a prodrug, derivative, pharmaceutical salt, or analog thereof) can be targeted for direct delivery to the liver, e.g., via infusion into the hepatic artery. Initial intravenous dosages are typically projected to be tenfold less than the oral dosages. Treatment is generally initiated with small dosages less than the optimum dose of the compound. Thereafter, the dosage is increased until the optimum effect under the circumstances is reached; precise dosages for oral, parenteral, nasal, or intrabronchial administration can be determined by the administering physician based on experience with the individual subject treated. Preferably, the pharmaceutical composition is in unit dosage form, e.g. as tablets or capsules. In such form, the composition is subdivided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g., corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, Poloxamer 188 surfactant, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine. Oral formulations herein may utilize standard delay or time-release formulations to alter the absorption of the active compound(s). The oral formulation can also consist of administering the active ingredient in water or a fruit juice, containing appropriate solubilizers or emulsifiers as needed.

Particularly suitable oral formulations for rapamycin 42-ester with 3-hydroxy-2-(hydroxymethyl)-2-methylpropionic acid are disclosed in U.S. Ser. No. 60/411,264 and PCT/US03/29228, which are hereby incorporated by reference. Such an oral formulation contains a granulation prepared using a wet granulation process. The granulation contains CCI-779, a water soluble polymer, a pH modifying agent, a surfactant, and an antioxidant. In one embodiment, the formulation contains from 0.1 to 30%, from 0.5 to 25%, from 1 to 20%, from 5 to 15%, or from 7 to 12% (wt/wt) CCI-779, from 0.5 to 50%, from 1 to 40%, from 5 to 35%, from 10 to 25%, or from 15 to 20% (wt/wt) water soluble polymer, from 0.5 to 10%, 1 to 8%, or 3 to 5% (wt/wt) surfactant, and from 0.001% to 1%, 0.01% to 1%, or 0.1% to 0.5% (wt/wt) antioxidant. However, other embodiments may contain more, or less, of these components.

The oral formulation may also contain suitable chelating agents, fillers, binders, surfactants, and the like to facilitate the granulation and tableting process. It is preferred that the wet granulation be performed with a hydroalcoholic solvent system comprising water and an alcohol, with ethanol being the preferred alcoholic component.

Typical water soluble polymers include, but are not limited to, polyvinylpyrrolidone (PVP), hydroxypropylmethylcellulose (HPMC), polyethylene glycol (PEG), and cyclodextrin or mixtures thereof. It is preferred that the water-soluble polymer is PVP, and having a molecular weight of between 2.5 and 60 kilodaltons. Any given oral formulation useful in the invention may contain multiple ingredients of each class of component. For example, an oral formulation containing an antioxidant may contain one or more antioxidants as the antioxidant component.

Acceptable pH modifying agents include, but are not limited to citric acid, sodium citrate, dilute HCl, and other mild acids or bases capable of buffering a solution containing CCI-779 to a pH in the range of about 4 to about 6. Acceptable antioxidants include, but are not limited to, citric acid, d,l-α-tocopherol, BHA, BHT, monothioglycerol, ascorbic acid, and propyl gallate. It is expected that the antioxidants of the oral formulations used in this invention will be used in concentrations ranging from 0.001% to 3% wt/wt. Chelating agents, and other materials capable of binding metal ions, such as ethylene diamine tetra acetic acid (EDTA) and its salts are capable of enhancing the stability of CCI-779. Surfactants may include polysorbate 80, sodium lauryl sulfate, sodium dodecyl sulfate, salts of bile acids (taurocholate, glycocholate, cholate, deoxycholate, etc.) that may be combined with lecithin. Alternatively, ethoxylated vegetable oils, such as Cremophor EL, vitamin E tocopherol propylene glycol succinate (Vitamin E TGPS), polyoxyethylene-polyoxypropylene block copolymers, and poloxamers. Binders, fillers, and disintegrants such as sucrose, lactose, microcrystalline cellulose, croscarmellose sodium, magnesium stearate, gum acacia, cholesterol, tragacanth, stearic acid, gelatin, casein, lecithin (phosphatides), carboxymethylcellulose calcium, carboxymethylcellulose sodium, methylcellulose, hydroxyethylcellulose, hydroxypropylcellulose, hydroxypropylmethycellulose phthalate, noncrystalline cellulose, cetostearyl alcohol, cetyl alcohol, cetyl esters wax, dextrates, dextrin, lactose, dextrose, glyceryl monooleate, glyceryl monostearate, glyceryl palmitostearate, polyoxyethylene alkyl ethers, polyethylene glycols, polyoxyethylene castor oil derivatives, polyoxyethylene stearates, and polyvinyl alcohol, and the like may also be incorporated into the oral formulation.

The oral formulation useful in the method of the invention can be prepared by preparing an alcoholic solution comprising CCI-779 and an antioxidant, and an aqueous solution comprising a water-soluble polymer, a surfactant, and a pH modifier, in sufficient quantity to adjust the pH of the aqueous solution to 4 to 6. Suitable alcohols include methanol, ethanol, isopropanol, and the like, where ethanol is the preferred alcohol. The solutions were mixed and added to a mixer containing intragranular excipients. Alternatively, the alcoholic and aqueous solutions can be added separately without mixing with each other. Such intragranular excipients comprise binders and fillers to promote dissolution enhancement. Typical intragranular excipients may include, but are not limited to, microcrystalline cellulose, lactose, and croscarmellose sodium. The solid intragranular excipients are granulated with the solutions in the mixer until a uniform granulation is achieved. The mixer can be a blender with intensifying bar, a low shear granulator or a high shear granulator. The granulation is dried in a fluid bed dryer at approximately 50° C., and milled using a suitable milling device, such as a Fitz mill. The wet granulation and drying can be done in a fluid bed granulator/dryer. The wet granulation can be dried using an tray drying oven. If desired, the dried granulation can be further blended with extragranular fillers and binders, such as microcrystalline cellulose, croscarmellose sodium, and magnesium stearate in a blender, such as a V-blender, before compression into tablets.

Alternatively, some of the water-soluble polymer can be contained in the intragranular excipients, and the aqueous and alcoholic solutions added to the mixer containing the intragranular excipients stepwise. For example, the order of addition to the mixer may be one half of the aqueous solution, followed by the entire alcoholic solution, and then the remainder of the aqueous solution. Other sequences of addition are possible and permissible in these solid oral formulations.

In some cases it may be desirable to administer the compounds directly to the airways in the form of an aerosol.

The compounds may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Particularly suitable injectable formulations for rapamycin 42-ester with 3-hydroxy-2-(hydroxymethyl)-2-methylpropionic acid are disclosed in U.S. patent application Ser. No. 10/626,943 and PCT/US03/223276, which are hereby incorporated by reference. In this embodiment, the injectable formulation useful in the invention provides a CCI-779 cosolvent concentrate containing an parenterally acceptable solvent and an antioxidant as described above and a parenteral formulation containing CCI-779, composed of CCI-779, an parenterally acceptable cosolvent, an antioxidant, a diluent solvent, and a surfactant. Any given formulation useful in this invention may contain multiple ingredients of each class of component. For example, a parenterally acceptable solvent can include a non-alcoholic solvent, an alcoholic solvent, or mixtures thereof. Examples of suitable non-alcoholic solvents include, e.g., dimethylacetamide, dimethylsulfoxide or acetonitrile, or mixtures thereof. "An alcoholic solvent," may contain one or more alcohols as the alcoholic solvent component of the formulation. Examples of solvents useful in the formulations invention include, without limitation, ethanol, propylene glycol, polyethylene glycol 300, polyethylene glycol 400, polyethylene glycol 600, polyethylene glycol 1000, or mixtures thereof. These cosolvents are particularly desirable because degradation via oxidation and lactone cleavage occurs to a lower extent for these cosolvents. Further, ethanol and propylene glycol can be combined to produce a less flammable product, but larger amounts of ethanol in the mixture generally result in better chemical stability. A concentration of 30 to 100% v/v of ethanol in the mixture is preferred.

In this embodiment, the stability of CCI-779 in parenterally acceptable alcoholic cosolvents is enhanced by addition of an antioxidant to the formulation. Acceptable antioxidants include, but are not limited to, citric acid, d,l-$\alpha$-tocopherol, BHA, BHT, monothioglycerol, ascorbic acid, propyl gallate, and mixtures thereof. Generally, the parenteral formulations useful in this embodiment of the invention will contain an antioxidant component(s) in a concentration ranging from 0.001% to 1% w/v, or 0.01% to 0.5% w/v, of the cosolvent concentrate, although lower or higher concentrations may be desired. Of the antioxidants, d,l-$\alpha$-tocopherol is particularly desirable and is used at a concentration of 0.01 to 0.1% w/v with a preferred concentration of 0.075% w/v of the cosolvent concentrate.

In certain embodiments, the antioxidant component of the formulation of the invention also exhibits chelating activity. Examples of such chelating agents include, e.g., citric acid, acetic acid, and ascorbic acid (which may function as both a classic antioxidant and a chelating agent in the present formulations). Other chelating agents include such materials as are capable of binding metal ions in solution, such as ethylene diamine tetra acetic acid (EDTA), its salts, or amino acids such as glycine are capable of enhancing the stability of CCI-779. In some embodiments, components with chelating activity are included in the formulations of the invention as the sole "antioxidant component". Typically, such metal-binding components, when acting as chelating agents are used in the lower end of the range of concentrations for the antioxidant component provided herein. In one example, citric acid enhanced the stability of CCI-779 when used at a concentration of less than 0.01% w/v. Higher concentrations are less stable solutions and thus, less desirable for products to be subject to long-term storage in liquid form. Additionally, such chelating agents may be used in combination with other antioxidants as part of the antioxidant component of the invention. For example, an acceptable formulation may contain both citric acid and d,l-α-tocopherol. Optimal concentrations for the selected antioxidant(s) can be readily determined by one of skill in the art, based upon the information provided herein.

Advantageously, in certain embodiments of the parenteral formulations useful in the invention, precipitation of CCI-779 upon dilution with aqueous infusion solutions or blood is prevented through the use of a surfactant contained in the diluent solution. The most important component of the diluent is a parenterally acceptable surfactant. One particularly desirable surfactant is polysorbate 20 or polysorbate 80. However, one of skill in the art may readily select other suitable surfactants from among salts of bile acids (taurocholate, glycocholate, cholate, deoxycholate, etc.) which are optionally combined with lecithin. Alternatively, ethoxylated vegetable oils, such as a pegylated castor oil [e.g., such as PEG-35 castor oil which is sold, e.g., under the name Cremophor EL, BASF], vitamin E tocopherol propylene glycol succinate (Vitamin E TGPS), and polyoxyethylene-polyoxypropylene block copolymers can be used in the diluent as a surfactant, as well as other members of the polysorbate family such as polysorbate 20 or 60 Other components of the diluent may include water, ethanol, polyethylene glycol 300, polyethylene 400, polyethylene 600, polyethylene 1000, or blends containing one or more of these polyethylene glycols, propylene glycol and other parenterally acceptable cosolvents or agents to adjust solution osmolarity such as sodium chloride, lactose, mannitol or other parenterally acceptable sugars, polyols and electrolytes. It is expected that the surfactant will comprise 2 to 100% w/v of the diluent solution, 5 to 80% w/v, 10 to 75% w/v, 15 to 60% w/v, and preferably, at least 5% w/v, or at least 10% w/v, of the diluent solution.

A parenteral formulation useful in the invention can be prepared as a single solution, or preferably can be prepared as a cosolvent concentrate containing CCI-779, an alcoholic solvent, and an antioxidant, which is subsequently combined with a diluent that contains a diluent solvent and suitable surfactant. Prior to use, the cosolvent concentrate is mixed with a diluent comprising a diluent solvent, and a surfactant. When CCI-779 is prepared as a cosolvent concentrate according to this invention, the concentrate can contain concentrations of CCI-779 from 0.05 mg/mL, from 2.5 mg/mL, from 5 mg/mL, from 10 mg/mL or from 25 mg/mL up to approximately 50 mg/ml. The concentrate can be mixed with the diluent up to approximately 1 part concentrate to 1 part diluent, to give parenteral formulations having concentrations of CCI-779 from 1 mg/mL, from 5 mg/mL, from 10 mg/mL, from 20 mg/mL, up to approximately 25 mg/ml. For example the concentration of CCI-779 in the parenteral formulation may be from about 2.5 to 10 mg/mL. This invention also covers the use of formulations having lesser concentrations of CCI-779 in the cosolvent concentrate, and formulations in which one part of the concentrate is mixed with greater than 1 part of the diluent, e.g., concentrate: diluent in a ratio of about 1:1.5, 1:2, 1:3, 1:4, 1:5, or 1:9 v/v and so on, to CCI-779 parenteral formulations having a CCI-779 concentration down to the lowest levels of detection.

Typically the antioxidant may comprise from about 0.0005 to 0.5% w/v of the formulation. The surfactant may for example comprise from about 0.5% to about 10% w/v of the formulation. The alcoholic solvent may for example comprise from about 10% to about 90% w/v of the formulation.

The parenteral formulations useful in this invention can be used to produce a dosage form that is suitable for administration by either direct injection or by addition to sterile infusion fluids for intravenous infusion.

For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semi-permeable membrane covering a reservoir containing the active ingredient with or without a carrier, or a matrix containing the active ingredient. Other occlusive devices are known in the literature.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

The documents identified in the specification are hereby incorporated by reference. A number of variations to the embodiments described herein will be obvious to those of skill in the art and are encompasses by the following claims.

What is claimed is:

1. A method of treating or inhibiting hepatic fibrosis in a mammal in need thereof, which comprises providing to said mammal an effective amount of a CCI-779.

2. The method according to claim 1, wherein CCI-779 is provided to said mammal by oral or intravenous infusion.

3. The method according to claim 1, wherein CCI-779 is provided to said mammal by administration of a prodrug, derivative, pharmaceutical salt or analog of CCI-779 that forms an effective amount of CCI-779 in the body.

4. The method according to claim 1, wherein CCI-779 is administered by direct targeting to the liver.

5. The method according to claim 1, wherein CCI-779 is provided to said mammal by oral dose.

6. A method of treating or inhibiting hepatic cirrhosis in a mammal in need thereof, which comprises providing to said mammal an effective amount of a CCI-779.

7. The method according to claim 6, wherein CCI-779 is provided to said mammal by oral or intravenous infusion.

8. The method according to claim 6, wherein CCI-779 is provided to said mammal by administration of a prodrug, derivative, pharmaceutical salt or analog of CCI-779 that forms an effective amount of CCI-779 in the body.

9. The method according to claim 6, wherein CCI-779 is administered by direct targeting to the liver.

10. The method according to claim 1, wherein CCI-779 is provided to said mammal by oral dose.

* * * * *

UNITED STATES PATENT AND TRADEMARK OFFICE
CERTIFICATE OF CORRECTION

PATENT NO. : 7,060,709 B2
APPLICATION NO. : 10/767824
DATED : June 13, 2006
INVENTOR(S) : Cooperstone et al.

It is certified that error appears in the above-identified patent and that said Letters Patent is hereby corrected as shown below:

(1) Claim 10, Col. 8, line 64, replace "claim 1," with -- claim 6, -- ;

Signed and Sealed this

Sixth Day of March, 2007

JON W. DUDAS
*Director of the United States Patent and Trademark Office*